(12) United States Patent
Farrell et al.

(10) Patent No.: US 8,647,645 B2
(45) Date of Patent: Feb. 11, 2014

(54) ENHANCED MOISTURE BARRIER IMMEDIATE RELEASE FILM COATING SYSTEMS AND SUBSTRATES COATED THEREWITH

(75) Inventors: Thomas P. Farrell, Warrington, PA (US); Jason Teckoe, Lansdale, PA (US)

(73) Assignee: BPSI Holdings, LLC, Wilmington, DE (US)

( * ) Notice: Subject to any disclaimer, the term of this patent is extended or adjusted under 35 U.S.C. 154(b) by 192 days.

(21) Appl. No.: 12/769,188

(22) Filed: Apr. 28, 2010

(65) Prior Publication Data

US 2010/0291183 A1 Nov. 18, 2010

Related U.S. Application Data

(60) Provisional application No. 61/177,380, filed on May 12, 2009.

(51) Int. Cl.
*A61K 47/10* (2006.01)

(52) U.S. Cl.
USPC ........... 424/400; 424/463; 424/474; 424/475; 424/482; 424/490; 424/497

(58) Field of Classification Search
USPC ......... 424/400, 443, 463, 474, 475, 482, 490, 424/497
See application file for complete search history.

(56) References Cited

U.S. PATENT DOCUMENTS

| | | | |
|---|---|---|---|
| 4,725,441 A | 2/1988 | Porter et al. | |
| 4,828,841 A | 5/1989 | Porter et al. | |
| 5,330,759 A | 7/1994 | Pagay et al. | |
| 5,567,768 A | 10/1996 | Amici et al. | |
| 5,885,617 A | 3/1999 | Jordan | |
| 6,039,976 A | 3/2000 | Mehra et al. | |
| 6,207,199 B1 | 3/2001 | Allen et al. | |
| 6,420,473 B1 | 7/2002 | Chittamuru et al. | |
| 6,448,323 B1 | 9/2002 | Jordan et al. | |
| 6,468,561 B1 | 10/2002 | Grillo et al. | |
| 6,579,953 B1 | 6/2003 | Gotsche et al. | |
| 2006/0134216 A1 | 6/2006 | Farrell et al. | |
| 2006/0147522 A1 | 7/2006 | Olmstead et al. | |
| 2006/0229383 A1 | 10/2006 | Noami et al. | |
| 2007/0134324 A1 | 6/2007 | Messadek | |
| 2008/0254112 A1 | 10/2008 | Klokkers et al. | |
| 2009/0004292 A1 | 1/2009 | Kumar et al. | |
| 2010/0273884 A1* | 10/2010 | Clouatre et al. | 514/574 |

FOREIGN PATENT DOCUMENTS

| | | |
|---|---|---|
| EP | 0180287 A2 | 5/1986 |
| EP | 0347024 A2 | 12/1989 |
| EP | 0567327 A2 | 10/1993 |
| WO | WO 0230402 A2 | 4/2002 |
| WO | WO 2005009386 A2 * | 2/2005 |
| WO | 2006111980 | 10/2006 |
| WO | WO 2008112124 A2 | 9/2008 |

OTHER PUBLICATIONS

Anderson et al., Coating of pharmaceutical tablets: the spray-pan method, J. Pharm. Pharmac., 1966, 18, 783-794.*
International Search Report and Written Opinion issued in PCT/US2010/32748 and dated Jun. 28, 2010.
Extended European Search Report (dated Mar. 26, 2013).

* cited by examiner

*Primary Examiner* — Michael G Hartley
*Assistant Examiner* — Robert Cabral
(74) *Attorney, Agent, or Firm* — Lucas & Mercanti, LLP

(57) ABSTRACT

The present invention is directed to immediate release film coating systems for use on oral dosage forms such as compressed tablets and other orally-ingestible substrates which have improved moisture barrier properties. The film coating systems can be applied either directly to a substrate or after the substrate has been coated with a subcoat. In preferred aspects, the moisture barrier film coating is prepared as a dry powder mixture containing polyvinyl alcohol, a polymer with pH dependent solubility, a plasticizer, a glidant, and, optionally, a detackifier, an alkalizing agent and a pigment. Film coating compositions containing an aqueous suspension of the powder mixtures, methods of applying the coatings to substrates and the coated substrates are also disclosed.

17 Claims, No Drawings

ENHANCED MOISTURE BARRIER IMMEDIATE RELEASE FILM COATING SYSTEMS AND SUBSTRATES COATED THEREWITH

CROSS-REFERENCE TO RELATED APPLICATION

This application claims the benefit of priority under 35 U.S.C. 119(e) from U.S. Patent Application Ser. No. 61/177,380 filed May 12, 2009, the contents of which are incorporated herein by reference incorporated by reference herein.

1. FIELD OF THE INVENTION

The present invention relates to immediate release film coatings having improved moisture barrier properties. The invention also relates to pharmaceutical substrates having such film coatings and methods of preparing the same.

2. DESCRIPTION OF THE PRIOR ART

Over the years, considerable effort has been expended to enhance the shelf life of dosage forms. The core formulation of the product can be adjusted to help ensure that the active ingredient is stable and compatible with other ingredients, or a coating can be applied to help protect the active from degradation associated with moisture or oxygen ingress from the local environment. Once a core formulation has been identified, a typical approach is to use a film coating to act as a bather to help protect the dosage form from its immediate environment, thus enhancing the stability of the dosage form and increasing the product shelf life.

U.S. Pat. No. 5,885,617 describes film coatings based on polyvinyl alcohol (PVA) and soya lecithin, which provide excellent moisture barrier properties.

U.S. Pat. No. 6,448,323 discloses film coatings comprising polyvinyl alcohol, talc and a plasticizer (polyethylene glycol or glycerin), which have very good but higher water vapor transmission rates than the '617 compositions, but, advantageously in certain applications, significantly higher maximum fluid delivery rates.

U.S. Pat. No. 6,420,473 describes enteric film coatings comprising an acrylic resin, an alkalizing agent and a film coating detackifier. These compositions do not disintegrate in simulated gastric fluid (0.1 N HCl), even under stressed conditions over a period of one hour.

KR patent 10-0758592 discloses dry film coating compositions having 15-60 wt % polyvinyl alcohol and 20-50 wt % enteric polymer. The disclosure states that when the amount of enteric polymer is less than 20 wt %, the compositions show deteriorated moisture barrier performance.

There is still a need to develop immediate release film coatings that simultaneously have both excellent moisture barrier properties and the highest possible fluid delivery rates, since such compositions would offer both the best functionality and most economical application rates.

3. SUMMARY OF THE INVENTION

One object of the present invention is to provide an immediate release film coating formulation that has moisture barrier properties that are at least on par with, i.e. substantially similar to, those of the '617 compositions while significantly improving the maximum fluid delivery rate versus the '617 compositions. It is a further object of this invention to provide orally-ingestible dosage forms coated with the inventive compositions that completely disintegrate in media of varying pH (i.e. between pH 1.2 and 6.8) in less than about 30 minutes.

In one aspect of the invention, there are provided dry powder mixtures useful in preparing immediate release film coating compositions for the pharmaceutical and related arts. The powder mixture or blend includes a combination of polymers, plasticizers, detackifiers, glidants and pigments. In preferred aspects of this invention, a combination of polymers is envisaged, wherein one of the polymers is polyvinyl alcohol and the other is a polymer that has pH-dependent solubility behavior.

In another aspect of the invention, there are provided film coating compositions containing suspensions of one or more powder mixtures described above. The suspensions preferably contain from about 10 to about 25% solids (non-water) content. Still further aspects include methods of coating orally-ingestible substrates with the coating suspension as well as the coated substrates prepared by these methods.

As a result of the present invention, several advantages and improvements over the prior art are realized. For example, the artisan is now able to provide film coated ingestible products with immediate release character and excellent moisture barrier properties with maximum fluid delivery rates significantly higher than those of prior art formulations having the lowest water vapor transmission rates (i.e. '617 compositions). Thus, it is possible to provide an immediate release film coating with excellent moisture protection and enhanced maximum fluid delivery rate.

It has been surprisingly found that addition of a polymer with pH dependent solubility into a formulation with polyvinyl alcohol can enhance the moisture barrier properties of film coatings without loss of immediate release characteristics in media of varying pH. In one embodiment of the invention, incorporation of a relatively low level of pH dependent solubility polymer, preferably between 1-15%, more preferably between 2-10%, and even more preferably between 4 and 8%, has been found to provide immediate release coating performance with enhanced moisture protection to the orally-ingestible edible substrates. Barrier protection is important for many types of orally-ingestible edible substrates, which are unstable in the presence of moisture. In light of the aforementioned KR patent 10-0758592 which indicated that levels of enteric polymer below 20% result in inferior moisture barrier protection, it was unexpected and surprising that the addition of small amounts of an enteric polymer, i.e. about 1-15%, to a film coating composition would cause a dramatic improvement in the moisture barrier properties relative to those associated with the product described in the aforementioned '323 patent.

In preferred aspects of this invention, an immediate release film coating is provided having a water vapor transmission rate (WVTR, also known as moisture vapor transmission rate-MVTR) of less than about 9 g $H_2O$/day/100 inches square, preferably less than about 6 g $H_2O$/day/100 inches square, and with a maximum fluid delivery rate of at least about 20 g/min in a 15" fully perforated pan. This combination of properties for an immediate release film coating system is clearly advantageous over existing marketed products.

4. DETAILED DESCRIPTION OF THE INVENTION

For purposes of the present invention, "orally-ingestible substrate" shall be understood to mean any pharmaceutically acceptable dosage form, e.g. tablet, capsule, caplet, etc. or any other veterinary or confectionary product capable of being taken via the oral route of administration. The substrate can include one or more active pharmaceutical ingredients (APIs) nutritional supplements, etc.

For purposes of the present invention, "dry powder" shall be understood to include powders which are relatively dry to the touch rather than powders which are essentially without moisture content.

For purposes of the present invention, "ambient temperature" shall be understood to mean temperatures generally in the range of from about 20° C. (68° F.) to about 30° C. (86° F.)+/−3° C.

A first aspect of the invention includes powder mixtures which are useful in preparing immediate release film coatings. The film coatings have excellent moisture barrier properties and are typically applied as aqueous suspensions to orally ingestible substrates such as compressed tablets and the like using pan coating or spraying techniques well known to those of ordinary skill. The inventive powder mixtures preferably include polyvinyl alcohol, a polymer with pH-dependent solubility, a plasticizer, a glidant, and optionally additional additives including alkalizing agents, detackifiers and pigments.

In most embodiments, the total amount of polymer, (PVA+ polymer with pH-dependent solubility) included in the powder mixtures of the present invention is from about 30 to about 70% by weight. In some preferred embodiments, it ranges from about 30 to about 60% and more preferably ranges from about 32 to about 55%.

The grades of polyvinyl alcohol found useful for this invention are those that comprise partially hydrolyzed polyvinyl acetate, which has a percentage of hydrolysis greater than about 86.5 mol % and preferably in the range of about 86.5 to 89 mol %. Preferably, the polyvinyl alcohol is micronized to an average size of about 200 microns or less to facilitate dissolution into water when forming the aqueous coating solution. Preferably, the polyvinyl alcohol can be dissolved in water at ambient temperatures. The preferred range of PVA in the inventive compositions is about 28-55% by weight of the dry film coating composition. In an alternative preferred embodiment, the amount of PVA in the inventive compositions is about 30-40% by weight of the dry film coating composition. The polymer with pH-dependent solubility is a polymer which can dissolve at one biorelevant pH (e.g. pH=6.8) but not at another (e.g. pH=1.2). A non-limiting list of suitable polymers with pH dependent solubility include, for example, those which are soluble within the generally accepted enteric range of about 4-7, such as methacrylic acid copolymers including: poly(methacrylic acid, methyl methacrylate) 1:1 sold, for example, under the Eudragit L100 trade name; poly(methacrylic acid, ethyl acrylate) 1:1 sold, for example, under the Eudragit L30D, Kollicoat MAE 30 DP and Eudragit L100-55 trade names; partially-neutralized poly (methacrylic acid, ethyl acrylate) 1:1 sold, for example, under the Kollicoat MAE-100P trade name; and poly(methacrylic acid, methyl methacrylate) 1:2 sold, for example, under the Eudragit S trade name. Additional polymers that are substantially insoluble at low pH (e.g. about 1.2) and soluble at higher pH (e.g. above about 5) and also found useful are polyvinylacetate phthalate (PVAP), PVAP coprocessed with titanium dioxide (PVAP-T), cellulose acetate phthalate (CAP), hydroxypropylmethyl cellulose acetate succinate (HPMC-AS) and hydroxypropylmethyl cellulose phthalate (HPMC-P).

Another category of useful polymers are those that are substantially insoluble above pH of about 5 but soluble at lower pH. These polymers are generally referred to as reverse enteric polymers. One particularly suitable reverse enteric polymer is poly(butyl methacrylate, 2-dimethylaminoethyl methacrylate, methyl methacrylate) 1:2:1 sold, for example, under the Eudragit E trade name.

Combinations of the previously mentioned pH dependent polymers as well as fully-formulated systems comprising one or more of the polymers may be utilized. Fully-formulated film coatings comprising polymers with pH-dependent solubility include Acryl-EZE (comprising Eudragit L100-55), Sureteric (comprising PVAP) and Chromateric (comprising Kollicoat MAE-100P) tradenames. The polymers with pH-dependent solubility or formulated coatings comprising them may be used such that the pH dependent polymers are in the range of 1-15%, preferably between 2-10%, and more preferably between 4 and 8% of the final dry film coating composition.

The plasticizer is preferably polyethylene glycol (PEG) or triethyl citrate (TEC). Preferred grades of PEG are those that exist in the solid state at ambient temperature including those with molecular weights from about 3000 to 8000 grams/mole.

The glidant is preferably talc. The glidant is principally used to help tablets flow over each other and so generate a smooth surface finish. The amount of glidant present will depend upon need, but can broadly range from about 9 to about 50% by weight, preferably, the range is from about 12 to about 40%, and, more preferably, from about 15 to about 30%.

The alkalizing agent may be sodium bicarbonate or other components such as known other bicarbonates, a carbonate, a phosphate, or a hydroxide of sodium or potassium, magnesium carbonate, magnesium hydroxide, ammonium carbonate, ammonium bicarbonate, calcium hydroxide, or mixtures thereof which can neutralize acidic moieties on the backbone of a polymer with pH-dependent solubility. Sodium or potassium salts are preferred in some aspects of the invention. Sodium bicarbonate is a preferred alkalizing agent. The alkalizing agent is used principally to maintain a fully soluble formulation, and to ensure the film coating solution/suspension does not require sieving before use. The amount of alkalizing agent, if included, will depend upon need, and is based upon the degree of neutralizing required in the formulation. As a broad range, this equates to between about 1 to about 6% by weight of the level of acrylic polymer with pH dependent solubility in the formulation. Preferably, the range is from about 2 to about 4% by weight of the level of acrylic polymer with pH dependent solubility in the formulation and more preferably from about 2 to about 3% by weight of the level of acrylic polymer with pH dependent solubility in the formulation. In cases where the polymer is PVAP or PVAP-T the amount of alkalizing agent is from about 8 to about 20%, preferably from about 10 to about 14%. In another an alternative embodiment, a separate alkalizing agent is avoided by using a partially neutralized grade of a pH dependent polymer. Partially neutralized poly(methacrylic acid, ethyl acrylate) 1:1, sold under the Kollicoat MAE-100P trade name is one such grade. However, in some other aspects of the invention, the alkalizing agent may be excluded altogether with no adverse effects.

The detackifier can be selected from among lecithins, stearic acid, polysorbates, glyceryl monostearate, poloxamers, fumed silica, bentonite, edible hydrogenated vegetable oils, monoglycerides, diglycerides, waxes and mixtures thereof. The detackifier is used principally to reduce the incidence of tablet-to-tablet sticking that can occur during the film coating of pharmaceutical tablets and the like using aqueous suspensions/dispersions based on the inventive compositions. The total amount of detackifier present will depend upon need, but can broadly range from about 4 to about 25% by weight. Preferably, the range is from about 6 to about 14% and more preferably from about 8 to about 12%.

The pigments may be any food or pharmaceutically approved colors, opacifiers or dyes. For example, the pigments may be aluminum lakes, iron oxides, titanium dioxide, natural colors or pearlescent pigments (e.g. mica based pigments sold under the Candurin tradename). Examples of such pigments are listed in U.S. Pat. No. 4,543,570, which is incorporated herein by reference. The pigments may be used in the powder mixtures in a range (by weight) from about 1 to about 40% pigment, preferably, from about 4 to about 32% and, more preferably, from about 7 to about 30%. It will be understood, however, that the amount of pigment employed in the powder mixtures of the invention is an amount which is sufficient or effective to impart the required appearance of the outer coating to the surface of the substrate to be coated.

Furthermore, the powder mixtures may also include supplemental or auxiliary ingredients typically found in film coatings. A non-limiting list of such adjuvants includes surfactants, suspension aids, sweeteners, flavorants, etc. and mixtures thereof. A preferred surfactant is sodium lauryl sulfate.

One of the keys to the present invention is the ability to impart improved moisture barrier properties to the surface of consumable articles. In this regard, the components in the powder mixtures must meet all government approved requirements for human consumption.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. If any of the powder formulation ingredients are liquids, they are added only after all of the dry ingredients have been sufficiently blended, and the combination of wet and dry ingredients is blended for an additional amount of time to ensure homogeneity once all of the liquid is introduced.

As mentioned above, batch sizes will vary upon need. A non-limiting list of suitable blending devices include diffusion blenders such as a cross flow, V-blender, or hub blender, available from Patterson-Kelly, or convection blenders, such as Ruberg or CVM blenders, available from Azo and Readco, respectively, may be used. Blending of the aforementioned formulation may also be achieved by processing ingredients into a granular form to produce a non-dusting granular coating composition by methods including, but not limited to, wet massing, fluid bed granulation, spray granulation and dry compaction, roller compaction or slugging. Other manners of blending will be apparent to those of ordinary skill.

For purposes of illustration and not limitation, an aqueous suspension having about 20% solids content can be formed by dispersing 80.0 grams of a blended powder mixture described hereinabove into 320.0 grams of ambient temperature water. The water is weighed into a suitable vessel, i.e. one with a diameter approximately equal to the depth of the final suspension. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 80 grams of dry film coating composition is added to the vortex at a rate where there is no excessive build up of dry powder. The speed and depth of the mixing blade is adjusted to avoid air being drawn into the suspension so as to avoid foaming.

The suspension is stirred at low speed, preferably 350 rpm or less, for a time sufficient to insure that a homogenous mixture is formed. Using the above batch size as a guide, about 45 minutes would be required. The suspension is then ready for spraying onto pharmaceutical substrates and the like. Those of ordinary skill will also realize that there are many ways of preparing a substantially homogenous mixture of the solids in water and that the scope of the invention is in no way dependent on the apparatus used.

In still further embodiments of the invention, there are provided orally-ingestible substrates having an enhanced moisture barrier and high maximum fluid delivery rate immediate release film coating as well as methods of coating ingestible substrates using the suspensions described herein. As will be described in the examples below, the methods include applying the enhanced moisture barrier and high maximum fluid delivery rate immediate release film coating compositions (suspensions) to a surface of an orally ingestible substrate. The film coating can be applied as part of a pan coating or spray coating process commonly used to coat such articles. The amount of coating applied will depend upon several factors, including the substrate to be coated, the apparatus employed to apply the coating, etc. In most aspects of the invention, however the substrates will be coated to a theoretical weight gain of from about 0.25 to about 5.0%. Preferably, the theoretical weight gain is from about 0.5 to about 4.0% and more preferably, the theoretical weight gain is from about 1.0 to about 3.0% by weight of said substrate.

As mentioned above, the coating solutions of the present invention may also include auxiliary ingredients in addition to the powder mixture and the water.

The coated orally-ingestible substrates described above can also be made to include a subcoat film coating between the orally-ingestible substrate and the enhanced barrier film coating. The subcoat selected is preferably based on an edible film coating composition that is compatible with and adheres to both the orally-ingestible substrate and the enhanced barrier coating. Thus, the artisan may choose from a wide variety of pharmaceutical or food-acceptable coatings for use as subcoats such as Opadry® brand products available from Colorcon, Inc. or others containing freely soluble cellulosic or PVA polymers in the present invention. The subcoat is also applied to the substrate to provide from about a 0.25 to about a 5% weight gain to the orally-ingestible substrate.

Regardless of the method employed or the specific materials included in the film coating compositions, the orally-ingestible substrates of the present invention preferably have a water vapor transmission rate of less than about 9 and preferably less than about 6 g/water/day/100 inches square and thus minimize hydrolytic degradation of moisture-sensitive APIs.

A non-limiting list of suitable substrates that can be coated with the inventive coating system include compressed tablets, caplets, cores including pharmaceuticals, nutraceuticals and dietary supplements as well as any other art-recognized orally ingestible core.

5. EXAMPLES

The following examples serve to provide further appreciation of the invention but are not meant in any way to restrict the effective scope of the invention. All ingredients are expressed as being by weight %.

Example 1

A preferred formulation for an inventive dry coating composition is the following:

| Component | Percent | grams |
|---|---|---|
| Polyvinyl alcohol (PVA) | 35.00 | 28.00 |
| Poly(methacrylic acid, ethyl acrylate) 1:1 (Eudragit L100-55) | 4.00 | 3.20 |
| Talc | 23.88 | 19.10 |
| PEG 3350 | 12.00 | 9.60 |
| Titanium dioxide | 20.00 | 16.00 |
| Blue #2 lake | 5.00 | 4.00 |
| Sodium bicarbonate | 0.12 | 0.09 |
| | 100.00 | 80.00 |

Formulation Preparation:

The film coating suspension was prepared by weighing all ingredients into a suitable-sized food processor/blender and blending for 5 minutes until a homogenous mixture was produced. The ingredients of this formulation were all dry powders, but in examples that follow, if any formulation ingredients are liquids, they were added to the dry mixture after the initial 5 minute blend time, and the total mixture was blended an additional 5 minutes after all liquid was introduced.

Formulation Hydration:

Eighty grams of the blended mixture was dispersed into 320.0 grams of ambient temperature water to make an aqueous coating suspension having 20% solids content. The water was weighed into a vessel with the diameter approximately equal to the depth of the final suspension. A low shear mixer was lowered into the water and turned on to create a vortex from the edge of the vessel down to just above the mixing blade to prevent entrapment of air. The 80 grams of dry film coating composition was added to the vortex at a rate where there was no excessive build up of dry powder. The speed and depth of the mixing blade was adjusted to avoid air being drawn into the suspension so as to avoid foaming. The suspension was stirred at low speed, preferably 350 rpm or less, for 45 minutes and was then ready for spraying onto substrates like pharmaceutical tablets or the like.

Formulation Coating:

A 1.5 kilogram batch size of 10 mm standard convex placebos was spray coated with the above described suspension in an O'Hara LabCoat II fully perforated side-vented coating pan equipped with a 15" insert and 1-Spraying Systems Schlick gun (model 931 fitted with 1.2 mm nozzle). The average coating parameters were: inlet temperature (IT) 65° C., exhaust temperature (ET) 48° C., coating bed temperature (BT) 45° C., airflow 250 cubic meters/hr, air pressure −0.1 in. of water, fluid delivery rate (FDR) 15 g/min, atomizing air pressure (AP) 1.5 bar, pan speed (PS) 22 rpm. A theoretical coating weight gain of 3.0% was applied to the tablets, and the coated tablets were smooth, non-tacky and glossy.

Determination of Maximum Fluid Delivery Rate (MFDR):

The maximum fluid delivery rate was determined using a 1.5 kilogram batch size of 10 mm standard convex placebos which were spray coated with the invention of this disclosure in an O'Hara LabCoat II fully perforated side-vented coating pan equipped with a 15" insert and I-Spraying Systems Schlick gun (model 931 fitted with 1.2 mm nozzle). The average coating parameters were: inlet temperature (IT) 65° C., exhaust temperature (ET) 48° C., coating bed temperature (BT) 45° C., airflow 250 cubic meters/hr, air pressure −0.1 in. of water, atomizing air pressure (AP) 1.5 bar, pan speed (PS) 22 rpm. The fluid delivery rate (FDR) was increased until the point where tablets were observed to complete a full revolution stuck to the surface of the pan. At this point, the spray rate was reduced to obtain a rate at which the tablets did not stick to the pan, and this spray rate was recorded as the maximum fluid delivery rate. The maximum fluid delivery rate for the formulation of this Example 1 was determined to be 21 g/min.

Water Vapor Transmission Rate (WVTR):

Water vapor transmission rate, (WVTR) also known as moisture vapor transmission rate (MVTR) rate data was generated by preparing a cast film sample from a dispersion onto a flat surface and then drying in a laboratory oven at 40° C. The aim was to generate a 100 micron thick film (0.1 mm) for further testing. Drying times varied depending on formula composition and solids content of the dispersion. If no obvious defects were present, a digital micrometer was used to ensure average film thickness was between 90 and 110 microns. The VTI WPA-100 unit was set for an initial drying phase where the sample was purged at 25° C. and 100 cc/min (dry N2) for 15 minutes, and then one side of the sample was flushed with nitrogen gas at 25° C./80% RH at a rate of 200 cc/min until a stable water transmission rate was determined through the sample. The water vapor transmission rate for Example 1 was identified as 4.8 g water/day/100 inches square.

Disintegration Test:

Disintegration testing was performed in accordance with the USP Disintegration Method. Six tablets were prepared as described previously and placed in a basket assembly and immersed in either purified water or simulated gastric fluid (0.1N HCl) for up to one hour. The basket was moved up and down at a rate of about 28-32 cycles/minute. The integrity of the tablets was evaluated throughout the testing period, and the time for the first and last tablet to disintegrate noted. These values were then used to determine the average disintegration time for the samples in each media. The average disintegration time for placebo coated cores with 3% weight gain of Example 1 in purified water was found to be 9 minutes 31 seconds, while in 0.1N HCl this was measured as 9 minutes 9 seconds. This confirms that the film coatings of the invention are suitable for use as immediate release coatings.

Examples 2-23

Additional formulations were prepared, dispersed in water and coated onto tablets as described in Example 1. The corresponding coated tablets were then tested by the same methods described in Example 1.

| Component | Example 2 % |
|---|---|
| Polyvinyl alcohol | 35.00 |
| Eudragit L100-55 | 4.00 |
| Triethyl citrate | 12.00 |

| -continued | |
|---|---|
| Sodium bicarbonate | 0.12 |
| Talc | 23.88 |
| Titanium dioxide | 20.00 |
| Blue #2 lake | 5.00 |
| Max spray rate (g/min) 15" insert | 20 |
| WVTR (g H2O/day/100 sq in) | 7.6 |
| Average Disintegration in purified water (min:sec) | 06:58 |
| Average Disintegration in 0.1N HCl (min:sec) | 06:49 |

| | Example | | | | | | |
|---|---|---|---|---|---|---|---|
| Component | 3 % | 4 % | 5 % | 6 % | 7 % | 8 % | 9 (control) % |
| Polyvinyl alcohol | 38.05 | 37.07 | 36.10 | 35.12 | 33.17 | 31.22 | 0.00 |
| Eudragit L100-55 | 0.98 | 1.95 | 2.93 | 3.90 | 5.85 | 7.80 | 38.61 |
| PEG 8000 | 12.00 | 11.99 | 11.98 | 11.97 | 11.95 | 11.93 | 11.85 |
| Sodium bicarbonate | 0.03 | 0.06 | 0.09 | 0.12 | 0.18 | 0.23 | 1.16 |
| Talc | 24.00 | 23.98 | 23.96 | 23.94 | 23.90 | 23.86 | 23.70 |
| Titanium dioxide | 19.96 | 19.96 | 19.96 | 19.96 | 19.96 | 19.96 | 19.75 |
| Blue #2 lake | 4.99 | 4.99 | 4.99 | 4.99 | 4.99 | 4.99 | 4.94 |
| Max fluid delivery rate (g/min) 15" insert | 20 | 20 | 22 | 17 | 15 | 16 | 20 |
| WVTR (g H2O/day/100 sq in) | 5.7 | 6.1 | 5.5 | 3.2 | 3.1 | 3.4 | 5.7 |
| Average Disintegration in purified water (min:sec) | 04:18 | 05:04 | 04:11 | 04:30 | 04:12 | 04:33 | 04:57 |
| Average Disintegration in 0.1N HCl (min:sec) | 04:33 | 05:40 | 04:05 | 04:20 | 05:10 | 03:54 | >60:00 |

| | Example | | | | | | |
|---|---|---|---|---|---|---|---|
| Component | 10 % | 11 % | 12 % | 13 % | 14 % | 15 % | 16 (control) % |
| Polyvinyl alcohol | 38.05 | 37.07 | 36.10 | 35.12 | 33.17 | 31.22 | 0.00 |
| Partially neutralized poly(methacrylic acid, ethyl acrylate) 1:1 (Kollicoat MAE100P) | 0.98 | 1.95 | 2.93 | 3.90 | 5.85 | 7.80 | 38.61 |
| PEG 8000 | 12.00 | 11.99 | 11.98 | 11.97 | 11.95 | 11.93 | 11.85 |
| Sodium bicarbonate | 0.03 | 0.06 | 0.09 | 0.12 | 0.18 | 0.23 | 1.16 |
| Talc | 24.00 | 23.98 | 23.96 | 23.94 | 23.90 | 23.86 | 23.70 |
| Titanium dioxide | 19.96 | 19.96 | 19.96 | 19.96 | 19.96 | 19.96 | 19.75 |
| Blue #2 lake | 4.99 | 4.99 | 4.99 | 4.99 | 4.99 | 4.99 | 4.94 |
| Max fluid delivery rate (g/min) 15" insert | 23 | 20 | 18 | 18 | 17 | 17 | 26 |
| WVTR (g H2O/day/100 sq in) | 5.7 | 3.9 | 5.9 | 3.9 | 3.4 | 3.5 | 3.2 |
| Average Disintegration in purified water (min:sec) | 04:20 | 04:35 | 04:34 | 05:05 | 04:15 | 04:33 | 04:21 |
| Average Disintegration in 0.1N HCl (min:sec) | 04:19 | 04:45 | 04:21 | 04:23 | 04:06 | 04:25 | >60:00 |

| | Example | | | |
|---|---|---|---|---|
| Component | 17 % | 18 % | 19 % | 20 % |
| Polyvinyl alcohol | 35.12 | 35.12 | 35.12 | 34.77 |
| Eudragit L100-55 | 3.90 | 3.90 | 3.90 | 3.86 |
| PEG 3350 | 12.00 | 12.00 | 12.00 | 11.88 |
| Sodium bicarbonate | 0.00 | 0.12 | 1.00 | 2.00 |
| Talc | 23.98 | 23.86 | 22.98 | 22.75 |
| Titanium dioxide | 20.00 | 20.00 | 20.00 | 19.80 |
| Blue #2 lake | 5.00 | 5.00 | 5.00 | 4.95 |
| Max fluid delivery rate (g/min) 15" insert | 22 | 21 | 23 | 24 |
| WVTR (g H2O/day/100 sq in) | 5.89 | 5.89 | 11.67 | 13.93 |
| Average Disintegration in purified water (min:sec) | 08:25 | 08:07 | 09:32 | 08:26 |
| Average Disintegration in 0.1N HCl (min:sec) | 08:17 | 08:06 | 09:31 | 07:11 |

-continued

| Components | Example 21 % | Example 22 % | Example 23 % |
|---|---|---|---|
| Polyvinyl alcohol | 30.6 | 30.6 | 30.6 |
| Eudragit L100-55 | 3.4 | 3.4 | 3.4 |
| PEG 3350 | 6 | 12 | 18 |
| Glyceryl monostearate | 2.5 | 2.5 | 2.5 |
| Sodium bicarbonate | 0.12 | 0.12 | 0.12 |
| Talc | 32.38 | 26.38 | 20.38 |
| Titanium dioxide | 20 | 20 | 20 |
| Blue #2 lake | 5 | 5 | 5 |
| Max fluid delivery rate (g/min) 15" insert | 19 | 24 | 29 |
| WVTR (g H2O/day/100 sq in) | 5.62 | 5.48 | 7.18 |
| Average Disintegration in purified water (min:sec) | 09:36 | 09:27 | 09:15 |
| Average Disintegration in 0.1N HCl (min:sec) | 09:22 | 08:35 | 09:31 |

| Components | Example 24 % |
|---|---|
| Polyvinyl alcohol | 35.12 |
| PVAP | 3.90 |
| PEG 3350 | 12.00 |
| Sodium bicarbonate | 0.12 |
| Talc | 32.38 |
| Titanium dioxide | 20.00 |
| Blue #2 lake | 5.00 |
| Max fluid delivery rate (g/min) 15" insert | 29 |
| WVTR (g H2O/day/100 sq in) | 7.1 |
| Average Disintegration in purified water (min:sec) | 08:22 |
| Average Disintegration in 0.1N HCl (min:sec) | 08:45 |

Example 25

The products and procedures of Example 1 are repeated except that hydroxypropylmethyl cellulose acetate succinate (HPMC-AS) is used to replace the poly(methacrylic acid, ethyl acrylate) 1:1.

Example 26

The products and procedures of Example 1 are repeated except that hydroxypropylmethyl cellulose phthalate (HPMC-P) is used to replace the poly(methacrylic acid, ethyl acrylate) 1:1.

Example 27

The products and procedures of Example 1 are repeated except that poly(butyl methacrylate, 2-dimethylaminoethyl methacrylate, methyl methacrylate) 1:2:1 (Eudragit E PO) is used to replace the poly(methacrylic acid, ethyl acrylate) 1:1.

It has been surprisingly observed that, through the minor addition of a polymer with pH dependent solubility, it is possible to obtain excellent moisture barrier performance and enhanced maximum fluid delivery rate without loss of disintegration behavior in either aqueous or acid media. It has further been found that utilizing a level of polymer with pH dependent solubility between 4-8 wt % offers most advantage in terms of excellent barrier properties and minimal impact on disintegration behavior or the cost of the formulation. This is a surprising result as it would be anticipated that a larger proportion of a polymer with pH dependent solubility would be required to achieve the enhanced moisture barrier properties of the film coating, and that at this elevated level it would potentially lead to an increase in the disintegration time for the tablet in low pH media.

It is worthy of note that formulations evaluated with a polymer with pH dependent solubility inclusion level of greater than 38% coated, such as in Examples 9 and 16, onto tablets with a 3% wt gain failed to disintegrate in acid media after 1 hour and offered no enhancement in the moisture barrier performance over that of the film coating obtained by an inclusion of polymer with pH dependent solubility at 4-8 wt %.

In a further surprising result, it has been observed that while the level of alkalizing agent used in the formulation has no impact on maximum fluid delivery rate or disintegration of placebo tablets in aqueous or acidic environment, it does have a significant impact on the barrier properties of the film coating, wherein the lower the level of alkalizing agent, the better the barrier properties of the film coating. However, when the amount of alkalizing agent exceeds the amounts described herein, i.e. about 6% or below, it can be seen that any advantages obtained by including the pH-dependent polymers is progressively lost.

It has also been found that when different levels of plasticizer (polyethylene glycol or triethyl citrate) with a glidant (talc) and detackifier (glyceryl monostearate) are utilized in unison, maximum fluid delivery rate is enhanced with minimal impact on barrier properties or disintegration rates.

It has further been observed that by utilizing polyvinylacetate phthalate as the polymer with pH dependent solubility, see Example 24, the WVTR properties of the formulation are lower than that associated with products corresponding to U.S. Pat. No. 6,448,323, with no impact on acid disintegration. It is noted that the maximum fluid delivery rate of the system obtained is excellent and comparable to that of formulation disclosed in the '323 patent.

Comparison to Prior Art

To provide evidence that the enhanced barrier and maximum fluid delivery rate of the inventive formulations of this disclosure are superior and preferred over the prior art, a series of evaluations were conducted on both prior art and instant film coating formulations. These evaluations and their methods are described in detail below.

Comparative Examples

In order to compare the performance data in the above tables for the formulas of this disclosure to other film coating systems well known in the art, the following comparative examples were prepared, film coated, and tested. Evaluations for maximum fluid delivery rate and moisture barrier properties are identified below.

Comparative Example

Opadry® AMB Systems of U.S. Pat. No. 5,885,617

Opadry® AMB-based systems, a product of Colorcon, were hydrated and film coated in an O'Hara LabCoat II equipped with a 15" insert using the same substrates and conditions as described in Example 1. The maximum fluid delivery rate of this formulation was determined to be 11 g/min, and the water vapor transmission rate for the film 6.4 g $H_2O$/day/100 inches square. The '617 patent described the maximum fluid delivery rate of the Opadry AMB system as being 25-30 g/min in a 24" pan and its barrier properties of the order of 6 g $H_2O$/day/100 inches square. These results are comparable with the findings in this disclosure given the difference is scale of the coating process. As seen from the summary table below, the inventive formulations provide substantially similar barrier and disintegration properties as the products described in the '617 patent but offer the desirable improvement of significantly improved fluid delivery rates thereover.

Comparative Example

Opadry® II Systems of U.S. Pat. No. 6,448,323

Opadry® II-based systems, also a product of Colorcon, were hydrated and film coated in an O'Hara LabCoat II equipped with a 15" insert using the same substrates and conditions as described in Example 1. The maximum fluid delivery rate of this formulation was determined to be 29 g/min, and the water vapor transmission rate for the film 13.5 g $H_2O$/day/100 inches square. The '323 patent described the maximum fluid delivery rate of the Opadry II system as being 60 g/min in a 24" pan and its moisture vapor transmission rate about 10 g $H_2O$/day/100 inches square. Again, these results are comparable with the findings in this disclosure given the difference is scale of the coating process.

Comparative Example

Acryl-EZE® Systems of U.S. Pat. No. 6,420,473

Acryl-EZE®-based systems, available from Colorcon were hydrated and film coated in an O'Hara LabCoat II equipped with a 15" insert using the same substrates and conditions as described in Example 1, except that the bed temperature had to be reduced to maintain 35° C., and air volume was increased to 350 cubic meters/hr. The maximum fluid delivery rate of this formulation was determined to be 25 g/min, and the water vapor transmission rate for the film 1.5 g $H_2O$/day/100 inches square. It was found that this coating formulation did not dissolve in 0.1N acid solution under standard disintegration testing conditions.

Summary Table

| Example | WVTR (g H2O/ day/100 sq in) | Max fluid delivery rate (g/min) 15" insert | Average Disintegration in purified water (min:sec) | Average Disintegration in 0.1N HCl (min:sec) |
|---|---|---|---|---|
| 1 | 4.8 | 21 | 09:31 | 09:09 |
| 2 | 7.6 | 20 | 06:58 | 06:49 |
| 3 | 5.7 | 20 | 04:18 | 04:33 |
| 4 | 6.1 | 20 | 05:04 | 05:40 |
| 5 | 5.5 | 22 | 04:11 | 04:05 |
| 6 | 3.2 | 17 | 04:30 | 04:20 |
| 7 | 3.1 | 15 | 04:12 | 05:10 |
| 8 | 3.4 | 16 | 04:33 | 03:54 |
| 9 | 5.7 | 20 | 04:57 | >60:00 |
| 10 | 5.7 | 23 | 04:20 | 04:19 |
| 11 | 3.9 | 20 | 04:35 | 04:45 |
| 12 | 5.9 | 18 | 04:34 | 04:21 |
| 13 | 3.9 | 18 | 05:05 | 04:23 |
| 14 | 3.4 | 17 | 04:15 | 04:06 |
| 15 | 3.5 | 17 | 04:33 | 04:25 |
| 16 | 3.2 | 26 | 04:21 | >60:00 |
| 17 | 5.9 | 22 | 08:25 | 08:17 |
| 18 | 5.9 | 21 | 08:07 | 08:06 |
| 19 | 11.7 | 23 | 09:32 | 09:31 |
| 20 | 13.9 | 24 | 08:26 | 07:11 |
| 21 | 5.6 | 19 | 09:36 | 09:22 |
| 22 | 5.5 | 24 | 09:27 | 08:35 |
| 23 | 7.2 | 29 | 09:15 | 09:31 |
| 24 | 7.1 | 29 | 08:22 | 08:45 |
| Comparative Examples | | | | |
| Opadry ® AMB | 6.4 | 11 | 08:09 | 08:20 |
| Opadry ® II | 13.5 | 29 | 05:51 | 05:56 |
| Acryl-EZE ® | 1.5 | 25 | 10:46 | >60:00 |

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. An orally-ingestible substrate coated with an aqueous suspension formed by mixing a dry powder composition comprising a) polyvinyl alcohol, b) a polymer with pH dependent solubility selected from the group consisting of methacrylic acid copolymers, cellulose acetate phthalate, hydroxypropylmethyl cellulose phthalate, hydroxypropylmethyl cellulose acetate succinate, poly(butyl methacrylate, 2-dimethylaminoethyl methacrylate, methyl methacrylate) 1:2:1 and combinations thereof, c) an alkalizing agent comprising sodium bicarbonate present in an amount up to about 6% by weight, calculated based upon the amount of polymer with pH dependent solubility, d) about 12 to about 40% by weight of a glidant and e) optionally a plasticizer; with water
    wherein the aqueous suspension is applied to the orally-ingestible substrate as a single coating layer, and the coated orally-ingestible substrate disintegrates in an aqueous medium of pH 1.2 in less than 30 minutes.

2. The coated orally-ingestible substrate of claim 1 wherein the dry powder composition further comprises a detackifier or a pigment.

3. The coated orally-ingestible substrate of claim 1 wherein the plasticizer is polyethylene glycol or triethyl citrate.

4. The coated, orally-ingestible substrate of claim 1 wherein the glidant is talc.

5. The coated orally-ingestible substrate of claim 1 wherein the polyvinyl alcohol comprises 28-55% by weight of the dry powder composition.

6. The coated orally-ingestible substrate of claim 5 wherein the polyvinyl alcohol comprises 30-40% by weight of the dry powder composition.

7. The coated orally-ingestible substrate of claim 1 wherein the polymer with pH dependent solubility comprises 1-15% by weight of the dry powder composition.

8. The coated orally-ingestible substrate of claim 7 wherein the polymer with pH dependent solubility comprises 2-10% by weight of the dry powder composition.

9. The coated orally-ingestible substrate of claim 8 wherein the polymer with pH dependent solubility comprises 4-8% by weight of the dry powder composition.

10. The coated orally-ingestible substrate of claim 1 wherein the glidant comprises from about 15 to about 30% by weight of the dry powder composition.

11. The coated orally-ingestible substrate of claim 1 wherein the amount of alkalizing agent is from about 2 to about 4% by weight, calculated based upon the amount of polymer with pH dependent solubility.

12. The coated orally-ingestible substrate of claim 1 wherein the amount of alkalizing agent is from about 2 to about 3% by weight, calculated based upon the amount of polymer with pH dependent solubility.

13. The coated orally-ingestible substrate of claim 1, wherein the film coating has a water vapor transmission rate of less than about 9 g $H_2O$/day/100 inches square.

14. A method of preparing a pharmaceutically acceptable coated oral solid dosage form, comprising: coating an orally-ingestible substrate with an aqueous film coating suspension formed by mixing a dry powder composition containing polyvinyl alcohol, a polymer with pH dependent solubility selected from the group consisting of methacrylic acid copolymers, cellulose acetate phthalate, hydroxypropylmethyl cellulose phthalate, hydroxypropylmethyl cellulose acetate succinate, poly(butyl methacrylate, 2-dimethylaminoethyl methacrylate, methyl methacrylate) 1:2:1 and combinations thereof, an alkalizing agent comprising sodium bicarbonate in an amount up to about 6% by weight, calculated based upon the amount of polymer with pH dependent solubility, about 12 to about 40% by weight of a glidant and optionally a plasticizer, with water, at a fluid delivery rate of at least about 15 g/min in a 15" fully perforated pan until a single layer of film coating is formed on said substrate having a water vapor transmission rate of less than about 9 g $H_2O$/day/100 inches square and the pharmaceutically acceptable coated oral solid dosage form disintegrates in an aqueous medium of pH 1.2 in less than 30 minutes.

15. The coated orally-ingestible substrate of claim 1 wherein the dry powder composition contains
   a) polyvinyl alcohol,
   b) a methacrylic acid copolymer,
   c) an alkalizing agent comprising sodium bicarbonate, present in an amount up to about 6% by weight, calculated based upon the amount of polymer with pH dependent solubility,
   d) about 12 to about 40% by weight talc, and optionally
   e) a plasticizer.

16. The coated orally-ingestible substrate of claim 1, wherein said substrate is selected from the group consisting of tablets, capsules, caplets, veterinary and confectionary products capable of being taken via the oral route of administration.

17. The coated orally-ingestible substrate of claim 1, wherein the methacrylic copolymer is a poly(methacrylic acid, ethyl acrylate).

* * * * *